United States Patent [19]

Francese et al.

[11] Patent Number: 4,701,569

[45] Date of Patent: Oct. 20, 1987

[54] PROCESS FOR THE PREPARATION OF PERFLUOROALKYLATED ALCOHOLS AND ESTERS

[75] Inventors: Catherine Francese, L'Hay les Roses; Marc Tordeux, Sceaux; Claude Wakselman, Paris, all of France

[73] Assignee: Rhone-Poulenc Specialties Chimiques, Courbevoie, France

[21] Appl. No.: 865,276

[22] Filed: May 21, 1986

[30] Foreign Application Priority Data

May 22, 1985 [FR] France ................................. 85 07696

[51] Int. Cl.$^4$ ............................................. C07C 33/46
[52] U.S. Cl. ..................................... 568/812; 568/715
[58] Field of Search ................................. 568/715, 812

[56] References Cited

U.S. PATENT DOCUMENTS 4,484,993 11/1984 Ishikawa et al. ..................... 568/812
4,603,227 7/1986 Hazen et al. ......................... 568/812

FOREIGN PATENT DOCUMENTS 0065233 4/1983 Japan ................................... 568/812
685133 12/1932 United Kingdom ................ 568/812

OTHER PUBLICATIONS

Kitazume et al., "Chemical Society of Japan, Chemical Letters", pp. 1679–1981 (1981).
English Translation of Japanese Patent to Daikin Kogyokk, JA 0065223 (Apr. 1983).
Chahoway et al., "J. Chem. Soc.", (1934), pp. 701–703.

Primary Examiner—Werren B. Lone
Attorney, Agent, or Firm—Finnegan, Henderson, Farabow, Garrett & Dunner

[57] ABSTRACT

A process for the preparation of perfluoroalkylated alcohols and esters by bringing a carbonyl-containing derivative and a perfluoroalkyl iodide or bromide into contact with zinc, preferably in the presence of a polar aprotic solvent and/or a pyridine.

20 Claims, No Drawings

PROCESS FOR THE PREPARATION OF PERFLUOROALKYLATED ALCOHOLS AND ESTERS

The present invention relates to a process for the preparation of perfluoroalkylated alcohols and esters. It particularly relates to a process of perfluoroalkylation of carbonyl compounds.

The attachment of trifluoromethyl iodides to carbonyl compounds in a polar aprotic solvent in the presence of zinc and ultrasonic waves, according to Kitazume and Ishikawa (Chemistry Letters, 1981, pages 1679–1680), is known. The authors affirm in this paper that in the absence of ultrasonic waves no reaction takes place. Since ultrasonic waves cannot be used in large-scale processes, this technique cannot therefore be retained on an industrial scale. Trials according to the same process have also been carried out with perfluoroethyl and propyl iodides (Solladie-Cavallo, Farkhani, Fritz, Lazrak and Suffert, Tetrahedron Letters, 25, 4117–4120, 1984).

The perfluoroalkylation of aldehydes by reacting perfluoroalkyl iodides with different aldehydes in the presence of catalysts chosen from palladium- or nickel-triphenylphosphine complexes according to O'Reilly, Maruta and Ishikawa, (Chemistry Letters, 517–520, 1984) is also known. The reaction can be used on an industrial scale but, economically, the cost of the catalyst makes this reaction difficult to use.

The object of the present invention is an industrially usable process. The invention relates to a process for the perfluoroalkylation of carbonyl compounds, comprising the step of reacting a carbonyl-containing derivative with a perfluoroalkyl iodide or bromide in the presence of zinc and the substantial absence of ultrasonic waves. Preferably, the reaction occurs in a polar aprotic solvent and/or a pyridine.

The invention also relates to a process for the perfluoroalkylation of carbonyl compounds, comprising the step of reacting a carbonyl-containing derivative with a perfluoroalkyl iodide, the alkyl chain of which contains from 2 to 12 carbon atoms, or a perfluoroalkyl bromide in the presence of zinc and preferably in the presence of a polar aprotic solvent and/or a pyridine.

The process of the present invention has the advantage, when compared to all processes known in the prior art, of not using catalysts or equipment which are impossible to employ industrially. Moreover, the process of the present invention can be carried out in the substantial absence of ultrasonic waves.

The perfluoroalkyl iodides or bromides are preferably chosen from perfluoroalkyl bromides, the perfluoroalkyl chain of which perferably contains from 1 to 12 carbon atoms, more preferably, trifluoromethyl bromide, and perfluoroalkyl iodides, the perfluoroalkyl chain of which preferably contains from 2 to 12 carbon atoms. This preference is not due to a difference in the reactivity of different compounds but rather to a difference in cost. Bromotrifluoromethane is much less expensive than iodotrifluoromethane and, conversely, perfluoroethyl, perfluorobutyl and similar iodides are much less expensive than their brominated analogues.

The carbonyl-containing derivatives preferably corresponds to the following general formula (I):

wherein R and R', which may be identical or different, are selected from the group consisting of hydrogen, straight-chain or branched alkyl or alkenyl groups containing 1 to 20 carbon atoms and preferably 1 to 12 carbon atoms, alicyclic or mono-, poly- or heterocyclic aromatic groups optionally substituted by a radical chosen from the constituents: hydroxyl, halogen, alkyl, preferably $C_1$–$C_6$ alkyl, alkenyl, preferably $C_1$–$C_6$ alkenyl, alkoxy, preferably $C_1$–$C_6$ alkoxy, alkylthio, preferably $C_1$–$C_6$ alkylthio, dialkylamino, preferably $C_1$–$C_6$ dialkylamino, nitrile, ester, amide, aryl, aryloxy, arylthio, fluoroalkyl, preferably $C_1$–$C_6$ fluoroalkyl, fluoroalkoxy, preferably $C_1$–$C_6$ fluoroalkoxy, and fluoroalkylthio, preferably $C_1$–$C_6$ fluoroalkylthio.

Illustrative compounds having the formula (I) include benzaldehydes such as methylbenzaldehydes, methoxybenzaldehydes, fluoro-, bromo- and chlorobenzaldehydes, cyanobenzaldehydes, dimethylaminobenzaldehydes, naphthalenecarbaldehydes, anthracenecarbaldehydes, pyridinecarbaldehydes, furfural, formaldehyde, acetaldehyde, propanal, butanal, cyclohexanecarbaldehyde, cinnamaldehyde, cyclohexanones, acetophenone and methyl or ethyl pyruvates.

For an advantageous implementation of the invention, a polar aprotic solvent and/or a pyridine is used.

Illustrative polar aprotic solvents which may be used in the process of the invention include dimethylformamide, dimethyl sulfoxide, dimethylacetamide, N-methylpyrrolidone and hexamethylphosphoramide.

Dimethylformamide and/or a pyridine is, or are, preferably employed.

Any pyridine may be chosen, whether unsubstituted or substituted, for example, by one or more alkyl groups, such as methyl- or dimethylpyridine. It is preferred, however, to use unsubstituted pyridine.

Pyridine makes it possible to reduce considerably the induction time of the reaction.

According to an advantageous implementation of the invention, a molar ratio of zinc to the carbonyl-containing derivative of more than or equal to 1 and less than 2, and a molar ratio of perfluoroalkyl iodide or bromide to the carbonyl-containing derivative of more than or equal to 1, are preferably used. If the perfluoroalkyl halide is used in excess and if the halide used is trifluoromethyl bromide, the latter will be easily recycled because it is in a gaseous form.

For a better implementation of the reaction, it is preferred to maintain a temperature of less than 115° C. and even more preferably a temperature of from −20° C. to 90° C.

The temperature will be adapted, by the person skilled in the art, to the product to be perhaloalkylated; thus, for example, a temperature of about 0° C. will be used for straight-chain aldehydes, a temperature of about 90° C. for formaldehyde and generally room temperature for all other compounds.

It is preferable to operate in the absence of oxygen.

The pressure is preferably greater than or equal to atmospheric pressure and is more preferably from 1 to 10 bars. Illustrative products obtained according to the process of the invention include 1-phenyl-2,2,2-trifluoroethanol, methyl-, methoxy-, fluoro-, chloro-, bromo-, cyano- and dimethylamino-substituted 1-phenyl-2,2,2-trifluoroethanols, 1-phenyl-2,2,3,3,3-pentafluoropropanol, 1-(1-naphthyl)-2,2,2- trifluoroethanol, 1-(9-anthryl)-2,2,2-trifluoroethanol, 1-pyridyl-2,2,2-trifluoroethanol, 1-(2-furfuryl)-2,2,2-trifluoroethanol, 2,2,2-trifluoroethyl benzoate, 1,1,1-trifluoro-2-butanol, 1-cyclohexyl-2,2,2-trifluoroethanol 4-phenyl-1,1,1-trifluoro-3- buten-2-ol, n-perfluorohexylphenylmethanol, 1,1,1-trifluoro-2-phenyl-2-propanol, 1-trifluoromethylcyclohexanol and methyl or ethyl 2-hydroxy-2-trifluoromethylpropionates.

The products obtained by the process of the present invention are used as synthesis intermediates in the pharmaceutical and plant protection industry, in the preparation of polymers (Hito, Macromolecule 1982, 15, 915), for the preparation of liquid crystals and for the separation of optical isomers (J. Organic Chemistry 42, 384, 1370, 1977).

The invention will be described in greater detail by means of the following examples, which should not be regarded as limiting the invention.

EXAMPLES 1 TO 9—BENZALDEHYDES 25 ml of pyridine, 10 ml of benzaldehyde (0.0985 mole) and 6.5 g of powdered zinc (0.1 mole) were placed in a thick glass flask.

The flask was placed in a Parr bomb. It was evacuated and then bromotrifluoromethane was introduced until a pressure of 2.6 bars was reached. The flask was shaken during the reaction period.

An exothermic reaction began about 5 minutes later.

The pressure of bromotrifluoromethane was maintained at between 3 and 1.5 bars during the reaction, which lasted approximately one hour.

The total quantity absorbed was 30 g (0.2 mole).

Filtration was carried out, followed by hydrolysis with 50 ml of ice-cold 10% hydrochloric acid and stirring for 30 minutes.

After extraction with ether and washing with water, the unreacted benzaldehyde was precipitated with sodium hydrogen sulfite.

This was carried out by shaking the ether phase to which the bisulfite reagent, prepared from 120 ml of a 38% sodium hydrogen sulfite solution and 30 ml of methanol, was added for one hour and then filtered and extracted with ether.

After drying over magnesium sulfate and evaporation of the solvent, 1-phenyl-2,2,2-trifluoroetanol was distilled under vacuum : b.p.=75°/12 mmHg. 9g (52%) were obtained (b.p.$_{lit.}$=84°-87°/14 mmHg). $^{19}$F NMR (CFCl$_3$ ext): −77.7 ppm (d, J$_{F-H}$=7.1 Hz)
$^1$H NMR (TMS int.): 7.5 ppm (Ar—H); 5 ppm (q, CH); and 3.5 ppm (OH)

The results for benzaldehydes substituted at position 4 are summarized in the following Table I:

TABLE 1

| Ex. | Substituent | Sample taken | Mass obtained | b.p. |
|---|---|---|---|---|
| 1 | H | 10 ml (0.0985 mol) | 9 g (52%) | 75°/12 mm |
| 2 | CH$_3$ | 11 ml (0.934 mol) | 9.4 g (53%) | (a) 86-90°/10 mm |
| 3 | CH$_3$O | 12 ml (0.0987 mol) | 9.5 g (47%) | 122°/13 mm |
| 4 | F | 10 ml (0.0933 mol) | 11 g (60%) | 74-76°/15 mm |
| 5 | Cl | 13 g (0.0929 mol) | 9 g (46%) | (b) 90-95°/12 mm |
| 6 | Br | 10 g (0.0541 mol) | 3 g (22%) | 88-90°/0.1 mm |

TABLE 1-continued

| Ex. | Substituent | Sample taken | Mass obtained | b.p. |
|---|---|---|---|---|
| 7 | CN | 12 g (0.0916 mol) | 8 g (43%) | m.p. = 89° C. |
| 8 | N(CH$_3$)$_2$ | 14 g (0.094 mol) | <10% | |
| 9 | NO$_2$ | 13 g (0.0861 mol) | 0 | |

(a) b.p.$_{lit.}$ = 102°/15 mm Hg
(b) b/p$_{lit.}$ = 80°/4 mm Hg

EXAMPLES 10 TO 16—BENZALDEHYDE AND SOLVENTS 25 ml of solvent, 10 ml of benzaldehyde (0.0985 mole) and 6.5 g of zinc (0.1 mole) were placed in a thick glass flask.

The flask was placed in a Parr bomb. It was evacuated, and then, bromotrifluoromethane was introduced until a pressure of 2.6 bars was reached. The pressure was maintained at from 3 to 1.6 bars during the reaction. The flask was shaken throughout the period of the reaction.

Filtration was carried out, followed by hydrolysis with 50 ml of ice-cold 10% hydrochloric acid and stirring for 30 minutes.

After extraction with ether and washing with water, the unreacted benzaldehyde was precipitated with sodium hydrogen sulfite, followed by filtration and extraction with ether.

After drying over magnesium sulfate and evaporation of the solvent, 1-phenyl-2,2,2-trifluoroethanol was obtained.

| EXAMPLES | SOLVENT | YIELD |
|---|---|---|
| 10 | Dimethylacetamide | 10% |
| 11 | Dimethylformamide | 25% |
| 12 | Dimethylsulfoxide | 30% |
| 13 | Hexamethylphosphoramide | 10% |
| 14 | N—methylpyrrolidone | 5% |
| 15 | 2-Picoline | 20% |
| 16 | pyridine + dimethyl sulfoxide 5 ml  25 ml | 35% |

EXAMPLE 17—BENZALDEHYDE—CF$_3$I 25 ml of pyridine, 10 ml of benzaldehyde (0.0985 mole) and 6.5 g of powdered zinc (0.1 mole) were placed in a thick glass flask.

The flask was placed in a Parr bomb. It was evacuated and then 24 g (0.122 mol) of iodotrifluoromethane were introduced.

The reaction started about 5 minutes later and was exothermic.

the procedure was continued as in Example 1.

After extraction with ether, washing with water, drying over magnesium sulfate and evaporation of the solvent, 1-phenyl-2,2,2-trifluoroethanol was distilled under vacuum: b.p.=75°/12 mm Hg. 5.8 g (33.5%) were obtained.

EXAMPLES 18—BENZALDEHYDE—C$_2$F$_5$I 25 ml of pyridine, 10 ml of benzaldehyde (0.0985 mole) and 6.5 g of powdered zinc (0.1 mole) were placed in a thick glass flask.

The flask was placed in a Parr bomb. It was evacuated and then 32 g (0.130 mole) of iodopentafluoroethane were introduced.

The reaction started about 5 minutes later and was exothermic.

The procedure was continuted as in Example 1.

After extraction with ether, washing with water, drying over magnesium sulfate and evaporation of the solvent, 1-phenyl-2,2,3,3,3-pentafluoropropanol was distilled under vacuum: b.p. =72°-75°/10 mm Hg. 6 g (27%) were obtained (b.p.$_{lit.}$=84°-85°/10 mm Hg). $^{19}$F NMR (CFCl$_3$ ext): −81 ppm (s, CF$_3$); −127.8 ppm (d.d, CF$_2$, J$_{F-F}$=274.5 Hz, J$_{F-H}$=15 Hz); −121.7 ppm (d.d, CF$_2$, J$_{F-H}$=9.4 Hz); $^1$H NMR (TMS int.): 7.4 ppm (Ar—H); 5.1 ppm (d.d, CH); 3 ppm (OH).

EXAMPLE 19—1-NAPHTHALENECARBALDEHYDE 25 ml of pyridine, 15 ml of 1-naphthalenecarbaldehyde (0.111 mole) and 7 g of powdered zinc (0.11 mole) were placed in a thick glass flask.

The procedure was carried out as in Example 1.

After extraction with ether, washing with water, drying over magnesium sulfate and evaporation of the solvent, 1-(1-naphthyl)-2,2,2-trifluoroethanol was distilled under vacuum: b.p.=116°-118°/1 mm Hg. 3.6 g (14%) were obtained. $^{19}$F NMR (CFCl$_3$ ext): −66.7 ppm (d, J$_{F-H}$=7 Hz); $^1$H NMR (TMS int.): 8.2-7.3 ppm (Ar—H); 5.8 ppm (q, CH); 3.3 ppm (OH).

EXAMPLE 20—9-ANTHRACENECARBALDEHYDE 25 ml of pyridine, 10 g of 9-anthracenecarbaldehyde (0.0485 mole) and 6.5 g of powdered zinc (0.1 mole) were placed in a thick glass flask.

The procedure was continued as in Example 1.

After extraction with ether, washing with water, drying over magnesium sulfate and evaporation of the solvent, 5 g (37%) of 1-(9-anthryl)-2,2,2-trifluoroethanol were obtained, and were then sublimed. M.p.=130°-131° C. (m.p.$_{lit.}$=142°-144° C.). $^{19}$F NMR (CFCl$_3$ ext): −74.7 ppm (d, J$_{F-H}$=8.5 Hz); $^1$H NMR (CD$_3$CN, TMS int.): 8.8-7.4 ppm (Ar—H); 6.8 ppm (q, CH); 3 ppm (OH).

EXAMPLE 21—2-PYRIDINECARBALDEHYDE 25 ml of pyridine, 10 ml of 2-pyridinecarbaldehyde (0.105 mole) and 6.5 g of powdered zinc (0.1 mole) were placed in a thick glass flask.

The procedure was continued as in Example 1.

After extraction with dichloromethane, washing with water, drying over magnesium sulfate and evaporation of the solvent, 12 g (65%) of 1-(2-pyridyl)-2,2,2-trifluoroethanol are obtained, and are then sublimed. M.p.=45.5° C. $^{19}$F NMR (CFCl$_3$ ext): −77.7 ppm (d, J$_{F-H}$=6.6 Hz) $^1$H NMR (TMS int.): 9-7.3 ppm (Ar—H); 6.1 ppm (OH); 5.2 ppm (q, CH).

EXAMPLE 22—FURFURAL 25 ml of pyridine, 10 ml of furfural (0.121 mole) and 8 g of powdered zinc (0.12 mole) were placed in a thick glass flask.

The flask was placed in a Parr bomb. It was evacuated and then bromotrifluoromethane was introduced until a pressure of 2.6 bars was reached.

The procedure was continued as in Example 1.

After extraction with ether, washing with water, drying over magnesium sulfate and evaporation of the solvent, 1-(2-furfuryl)-2,2,2-trifluoroethanol was distilled under vacuum: b.p.=60°/12 mm Hg. 5.2 g (26%) were obtained. $^{19}$F NMR (CFCl$_3$ ext): −77.7 ppm (d, J$_{F-H}$=7.1 Hz); $^1$H NMR (TMS int.): 7.4-6.2 ppm (Ar—H); 4.9 ppm (q, CH); 3.5 ppm (OH).

EXAMPLE 23—FORMALDEHYDE 50 ml of pyridine, 5 g of formaldehyde (0.167 mole) and 11 g of zinc (0.169 mole) were placed in a thick glass flask.

The flask was placed in a Parr bomb. It was evacuated, heated to 90° C., and then bromotrifluoromethane was introduced until a pressure of 2.6 bars was reached. The flask was shaken.

The reaction started about 30 minutes later and the pressure of bromotrifluoromethane was maintained from 3 to 1.5 bars during the reaction, which lasted for about 2 hours.

Filtration was carried out, followed by the addition of 10 ml of benzoyl chloride. The reaction was exothermic. Hydrolysis with 10 ml of ice-cold 10% hydrochloric acid and extraction with ether were carried out. After evaporation of the solvent, 2,2,2-trifluoroethyl benzoate was purified by thin layer chromatography. 3.5 g (10%) were obtained.

2,2,2-Trifluoroethyl benzoate:

$^{19}$F NMR (CFCl$_3$ ext): −73 ppm (t, J$_{F-H}$=9.4 Hz); $^1$H NMR (TMS int.): 8.9-7.3 ppm (Ar—H); 4.7 ppm (q, CH$_2$).

EXAMPLE 24—BUTANAL 25 ml of pyridine, 10 ml of butanal (0.113 mole) and 8 g of zinc (0.123 mole) were placed in a thick glass flask.

The flask was placed in a Parr bomb. It was evacuated, cooled to 0° C., and then bromotrifluoromethane was introduced until a pressure of 2.6 bars was reached.

The reaction started about 5 minutes later and was exothermic. The pressure of bromotrifluoromethane was maintained at from 3 to 1.5 bars during the reaction, which proceeded for about one half hour. The flask was shaken throughout the period of reaction.

Filtration was carried out, followed by hydrolysis with 15 ml of 20% sulfuric acid for 8 hours.

After extraction with ether, washing with water, drying over magnesium sulfate and evaporation of the solvent, 1,1,1-trifluoro-2-pentanol was distilled: b.p.=92°-94°/760 mm Hg. 4.8 g (30%) were obtained. $^{19}$F NMR (CFCl$_3$ ext.): −79.5 ppm (d, J$_{F-H}$=7.5 Hz); $^1$NMR (TMS int.): 3.9 ppm (m, CH); 3.2 ppm (OH); 2.7-1.3 ppm (m, CH$_2$—CH$_2$); 1.2-0.8 ppm (m, CH$_3$).

EXAMPLE 25—CYCLOHEXANECARBALDEHYDE 25 ml of pyridine, 10 ml of cyclohexanecarbaldehyde (0.0827 mole) and 6.5 g of powdered zinc (0.1 mole) were placed in a thick glass flask.

The procedure of Example 1 was carried out.

After extraction with ether, washing with water, drying over magnesium sulfate and evaporation of the solvent, 1-cyclohexyl-2,2,2-trifluoroethanol was distilled under vacuum: b.p.=60°-64°/12 mm Hg. 4.5 g (30%) were obtained. $^{19}$F NMR (CFCl$_3$ ext): −75.5 ppm (d, J$_{F-H}$=7.7 Hz); $^1$H NMR (TMS int.): 4.1-3.4 (m, CH); 2.5 ppm (OH); 2.2-0.9 ppm (m, 10 H).

EXAMPLE 26—CINNAMALDEHYDE 25 ml of pyridine, 12 ml of cinnamaldehyde (0.0955 mole) and 6.5 g of powdered zinc (0.1 mole) were placed in a thick glass flask.

The procedure was continued as in Example 1.

After extraction with ether, washing with water, drying over magnesium sulfate and evaporation of the solvent, 4-phenyl-1,1,1-trifluoro-3-buten-2-ol was distilled under vacuum: b.p.=98°-102°/0.5 mm Hg. 10.5 g (55%) were obtained (b.p.$_{lit.}$=86-88/5 mm Hg). $^{19}$F NMR (CFCl$_3$ ext): −77.7 ppm (d, J$_{F-H}$=6.6 Hz); $^1$H NMR (TMS int.): 7.4 ppm (Ar—H); 6.9 ppm (d, CH, J$_{trans}$=16 Hz), 6.2 ppm (d, d, CH, J$_{trans}$=16 Hz, J$_{H,H}$=6 Hz); 4.7 ppm (q, CH); 3.6 ppm (OH).

EXAMPLE 27—BENZALDEHYDE—C$_6$F$_{13}$I 10 ml pyridine, 2 ml of benzaldehyde (0.0197 mole) and 2 g of powdered zinc (0.03 mole) were placed in a round-bottom flask. The flask was purged with argon and 10 g of 1-iodo-n-perfluorohexane (0.022 mole) were added with shaking. The reaction was exothermic. Filtration was carried out, followed by hydrolysis with 10 ml of ice-cold 10% hydrochloric acid while stirring for 30 minutes.

After extraction with ether and washing with water, the unreacted benzaldehyde was precipitated with sodium hydrogen sulfite. This was carried out by shaking the ether phase, to which 38% of sodium hydrogen sulfite and 30 ml of methanol have been added, for 1 hour, and then filtering and extracting with ether.

After drying over magnesium sulfate and evaporation of the solvent, 4 g (48%) of n-perfluorohexylphenylmethanol were obtained, which were then sublimed. M.p.=47° C. (m.p.$_{lit.}$=49°-51° C.). $^{19}$F NMR (CFCl$_3$ ext.): −79.7 ppm (t.t, CF$_3$); −115 and −125 ppm (d,d, CF$_2$, J$_{F-F}$=273 Hz); −118-122 ppm and −124−125 ppm (m, 8 F). $^1$H NMR (TMS int.): 7.5 ppm (Ar—H); 5.4-5.2 ppm (d.d, CH,$^3$J$_{F-H}$=17 Hz, $^3$J$_{F-H}$=8 Hz), 3.8 ppm (OH).

EXAMPLE 28—ACETOPHENONE 25 ml of pyridine, 10 g of acetophenone (0.0833 mole) and 6.5 g of powdered zinc (0.1 mole) were placed in a thick glass flask.

The flask was placed in a Parr bomb. It was evacuated, and then bromotrifluoromethane was introduced until a pressure of 2.6 bars was reached; the latter being maintained at from 3 to 1.5 bars during the reaction, which proceeded for about 3 hours. The flask was shaken throughout the reaction.

Filtration was carried out, followed by hydrolysis with 50 ml of ice-cold 10% hydrochloric acid and stirring for 30 minutes.

After extraction with ether, washing with water, drying over magnesium sulfate and evaporation of the solvent, 1,1,1-trifluoro-2-phenyl-2-propanol was purified by gas chromatography (column: 10% dinonyl phthalate on chromosorb WDMCS-60/80 mesh) at 145° C. $^{19}$F NMR (CFCL$_3$ ext.): −80 ppm (s, CF$_3$) $^1$H NMR (TMS inst.): 6.8-6.3 ppm (Ar—H); 1.9 ppm (OH); 0.9 ppm (s, CH$_3$).

EXAMPLE 29—CYCLOHEXANONE 25 ml of pyridine, 10 g of cyclohexanone (0.102 mole) and 7 g of powdered zinc (0.108 mole) were placed in a thick glass flask.

The flask was placed in a Parr bomb. It was evacuated, and then bromotrifluoromethane was introduced until a pressure of 2.6 bars was reached; the latter was maintained from 3 to 1.5 bars during the reaction, which proceeded for about 3 hours. The flask was shakaen throughout the period of the reaction.

Filtration was carried out, followed by hydrolysis with 50 ml of ice-cold 10% hydrochloric acid and stirring for 30 minutes.

After extraction with ether, washing with water, drying over magnesium sulfate and evaporation of the solvent, 1-trifluoromethylcyclohexanol was purified by gas chromatography (column: 10% dinonyl phthalate on chromosorb WDMCS 60/80 mesh) at 120° C. 3.4 g (20%) were obtained. $^{19}$F NMR (CFCl$_3$ ext.): −83 ppm (s, CF$_3$).

EXAMPLE 30—ETHYL PYRUVATE 25 ml of pyridine, 10 ml of ethyl pyruvate (0.0914 mole) and 6.5 g of powdered zinc (0.1 mole) were placed in a thick glass flask.

The flask was placed in a Parr bomb. It was evacuated, and then bromotrifluoromethane was introduced until a pressure of 2.6 bars was reached. The flask was shaken throughout the period of the reaction.

The reaction began about 5 minutes later and was exothermic. The pressure of bromotrifluoromethane was maintained at from 3 to 1.5 bars during the reaction, which lasted for about one half hour.

Filtration was carried out, followed by hydrolysis with 30 ml of ice-cold 10% hydrochloric acid.

After extraction with ether, washing with water, drying over magnesium sulfate and evaporation of the solvent, ethyl 2-hydroxy-2-trifluoromethylpropionate was distilled under vacuum. B.p.=60°/65 mm Hg. 6 g (35%) were obtained. (B.p.$_{lit.}$=140°-142°/760 mm Hg. $^{19}$F NMR (CFCl$_3$ ext.): −79.7 ppm (s, CF$_3$). $^1$H NMR (TMS int.): 4.6 ppm (q, CH$_2$, $^3$J$_{H-H}$=7 Hz); 4.2 ppm (OH 1.7 ppm (s, CH$_3$); 1.5 ppm (t, CH$_3$).

We claim:

1. A process for the perfluoroalkylation of carbonyl compounds, comprising the step of reacting a carbonyl-containing derivative with a perfluoroalkyl iodide or bromide in the presence of zinc and in the substantial absence of ultrasonic waves.

2. The process of claim 1, wherein said reaction occurs in a polar aprotic solvent and/or a pyridine.

3. The process of claim 1, wherein the perfluoroalkyl bromide is bromotrifluoromethane.

4. A process for the perfluoroalkylation of carbonyl compounds, comprising the step of reacting a carbonyl-containing derivative with a perfluoroalkyl iodide, the perfluoroalkyl chain of which contains 2 to 12 carbon atoms, or a perfluoroalkyl bromide in the presence of zinc.

5. The process of claim 4, wherein said reaction occurs in a polar aprotic solvent and/or a pyridine.

6. The process of claim 5, wherein the carbonyl-containing derivative corresponds to the formula (I):

wherein R and R', which may be identical or different, are selected from the group consisting of hydrogen, straight-chain or branched alkyl or alkenyl groups containing 1 to 20 carbon atoms, and alicyclic or mono-, poly-, or heterocyclic aromatic groups, wherein said alicyclic and aromatic groups may be substituted by a radical selected from the group consisting of hydroxyl, halogen, alkyl, alkenyl, alkoxy, alkylthio, dialkylamino, nitrile, ester, amide, aryl, aryloxy, arylthio, fluoroalkyl, fluoroalkoxy and fluoroalkylthio.

7. The process of claim 6, wherein in the formula (I), R is selected from the group consisting of straight-chain or branched alkyl or alkenyl groups containing 1 to 12 carbon atoms.

8. The process of claim 1, wherein the carbonyl-containing derivative corresponds to the formula (I):

wherein R and R', which may be identical or different, are selected from the group consisting of hydrogen, straight-chain or branched alkyl or alkenyl groups containing 1 to 20 carbon atoms, and alicyclic or mono-, poly-, or heterocyclic aromatic groups, wherein said alicyclic and aromatic groups may be substituted by a radical selected from the group consisting of hydroxyl, halogen, alkyl, alkenyl, alkoxy, alkylthio, dialkylamino, nitrile, ester, amide, aryl, aryloxy, arylthio, fluoroalkyl, fluoroalkoxy and fluoroalkylthio.

9. The process of claim 8, wherein in the formula (I), R is selected from the group consisting of straight-chain or branched alkyl or alkenyl groups containing 1 to 12 carbon atoms.

10. The process of claim 2, wherein the polar aprotic solvent is selected from the group consisting of dimethylformamide, dimethyl sulfoxide, dimethylacetamide, N-methylpyrrolidone and hexamethylphosphoramide.

11. The process of claim 10, wherein the polar aprotic solvent is dimethylformamide and wherein the reaction takes place in the presence of a pyridine.

12. The process of claim 11, wherein said pyridine is selected from the group consisting of pyridine and the alkylpyridines.

13. The process of claim 5, wherein the polar aprotic solvent is selected from the group consisting of dimethylformamide, dimethyl sulfoxide, dimethylacetamide, N-methylpyrrolidone and hexamethylphosphoramide.

14. The process of claim 13, wherein the polar aprotic solvent is dimethylformamide and wherein the reaction also takes place in the presence of a pyridine.

15. The process of claim 14, wherein said pyridine is selected from the group consisting of pyridine and the alkylpyridines.

16. The process of claim 1, wherein the molar ratio of zinc to the carbonyl-containing derivative is at least 0.9 but less than 2.1.

17. The process of claim 1, wherein the molar ratio of the perfluoroalkyl iodide or bromide to the carbonyl-containing derivative is at least 1.

18. The process of claim 4, wherein the molar ratio of zinc to the carbonyl-containing derivative is at least 0.9 but less than 2.1.

19. The process of claim 4, wherein the molar ratio of the perfluoroalkyl iodide or bromide to the carbonyl-containing derivative is at least 1.

20. The process of claim 4, wherein perfluoroalkyl bromide is bromotrifluoromethane.

* * * * *

UNITED STATES PATENT AND TRADEMARK OFFICE
CERTIFICATE OF CORRECTION

PATENT NO. : 4,701,569

DATED : October 20, 1987

INVENTOR(S) : Catherine FRANCESE, et al.

It is certified that error appears in the above-identified patent and that said Letters Patent is hereby corrected as shown below:

In Claim 20, Column 10, Line 1; change

"wherein perfluoroalkyl" to

--wherein the perfluoroalkyl--

Signed and Sealed this

Twenty-sixth Day of April, 1988

Attest:

DONALD J. QUIGG

Attesting Officer      Commissioner of Patents and Trademarks